United States Patent [19]

Kuntz

[11] 4,219,677
[45] Aug. 26, 1980

[54] TELOMERIZATION PROCESS
[75] Inventor: Emile Kuntz, Lyon, France
[73] Assignee: Rhone-Poulenc Industries, Paris, France
[21] Appl. No.: 926,127
[22] Filed: Jul. 19, 1978

Related U.S. Application Data
[62] Division of Ser. No. 817,800, Jul. 21, 1977, Pat. No. 4,142,060.

[30] Foreign Application Priority Data
Jul. 27, 1976 [FR] France .................................. 76 22824
[51] Int. Cl.² ........................................... C07C 41/10
[52] U.S. Cl. .................................... 568/657; 568/655; 568/656; 568/689; 568/690; 252/431 C
[58] Field of Search ............... 568/689, 690, 657, 655, 568/656; 252/431 C

[56] References Cited
U.S. PATENT DOCUMENTS
4,142,060  2/1979  Kuntz .................................. 568/840

FOREIGN PATENT DOCUMENTS
47-20604  6/1972  Japan ........................................ 568/690
1248593  10/1971  United Kingdom ..................... 568/690

Primary Examiner—John M. Ford
Assistant Examiner—R. W. Ramsuer
Attorney, Agent, or Firm—Burns, Doane, Swecker & Mathis

[57] ABSTRACT

A process for the telomerization of dienes with a telomerizing compound containing a mobile hydrogen atom is disclosed wherein the reaction between the diene and the telomerizing agent is effected in the presence of a catalytic system comprising a water-soluble sulfonated triaryl phosphine compound, preferably a water-soluble salt of a mono-, di-, or trisulfonated triphenyl phosphine and a transition metal compound, preferably palladium or a palladium-containing compound. Water is added either before or after the reaction is completed and the reaction products can easily be separated from the aqueous catalyst solution.

44 Claims, No Drawings

TELOMERIZATION PROCESS

This is a division of application Ser. No. 817,800, filed July 21, 1977, now U.S. Pat. No. 4,142,060, issued Feb. 27, 1974.

BACKGROUND OF THE INVENTION

1. Field of the Invention

The invention relates to a process for telomerizing olefins, especially dienes, with a telomerizing compound containing at least one mobile hydrogen atom, particularly to a process wherein the amount of the diene is at least equivalent to the amount of mobile hydrogen atoms.

2. Description of the Prior Art

The French Pat. No. 2,045,369 discloses a process for preparing diolefinic alcohols containing twice the number of carbon atoms of the starting 1,3-diolefins. According to this process, a reaction mixture is formed containing the diolefin, water, and a solvent wherein the diolefin, as well as the water are at least partially soluble in the presence of a catalyst containing palladium or platinum, phosphine and carbon dioxide gas as a co-catalyst. The diolefinic alcohol is formed by the reaction of the diolefin with water. For use in this type of process, such solvents are selected which have a certain affinity for the diene and for the water in order to maintain a liquid and homogeneous reaction mixture. The solvents which are used are organic solvents such as, e.g., dioxane, dimethyl acetamide, tert. butanol and acetone.

Processes for telomerizing diolefins, particularly butadiene, with various compounds containing mobile hydrogen atoms, such as alcohols, carbocyclic acids, silanols, ammonia, amines, compounds with reactive methylene groups, and the like, in the presence of a catalyst usually containing palladium and a co-catalyst, such as phosphine, are known in the art [see *Accounts Chem. Res.*, 1973, 6(1) 8–15].

The first major problem which arises during carrying out the prior art processes is the separation of the reaction products and the catalyst. It is, in effect, desirable to recover the catalyst for re-utilization. Yet the prior art proposes only processes wherein the final separation step has never been satisfactorily solved by a generally applicable method. It proves always to be difficult and incomplete. In effect, in most of the cases, not all of the reaction products can be separated from the reaction medium by simple methods since on the one hand, the catalyst is soluble in the organic solvents which are used and on the other hand, certain by-products are too nonvolatile to be separated by distillation. If it is possible to separate the main reaction product by distillation, for reasons concerning the thermal stability of the catalyst, it is impossible to eliminate the by-products, such as, oligomers and telomers of the diolefin, by distillation.

According to the prior art processes, a loss in catalyst is noted and the latter is present in the reaction product.

In case the compound containing the mobile hydrogen atom is water, the second major problem is how to exalt its reactivity. The solutions provided by the prior art exist in, e.g., adding an alcohol to the reaction mixture (British Pat. No. 1,354,507 and U.S. Pat. No. 3,670,032). A large amount of carbon dioxide gas has been used to increase the reaction speed (French Pat. No. 2,045,369, cited above). In the first case, the major inconvenience is the joint formation of undesirable ether (often even as the major product). In the second case, the amount of carbon dioxide has to be continuously recycled for economical reasons. Furthermore, the separation problems outlined above remain.

SUMMARY OF THE INVENTION

It is an object of the present invention to provide an improved process for reacting a diene with a compound containing a mobile hydrogen, which avoids these difficulties attendant the state of the art.

It is a further object of the present invention to provide such a process which permits an easy separation of the catalyst and the reaction products, e.g., by simple decantation or extraction, especially a process which avoids the contamination of the reaction product with impurities from the catalysts and avoids the loss of expensive catalyst.

It is a special object of the present invention to provide such a process wherein the catalyst can easily be recovered in a form which can be directly re-used for the same reaction, e.g., which can be directly recycled into the reaction mixture.

In order to accomplish the foregoing objects according to the present invention there is provided a process for telomerizing dienes, which comprises the step of reacting a diene with a telomerizing compound containing at least one mobile hydrogen atom in the presence of a water-soluble catalytic system comprising at least one water-soluble phosphine having the formula (I)

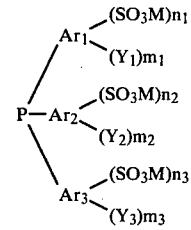

wherein $Ar_1$, $Ar_2$ and $Ar_3$ each represent an aryl group having from 6 to 10 carbon atoms, which may be alike or different from each other; $Y_1$, $Y_2$ and $Y_3$, which may be alike or different from each other each represent an alkyl group containing 1 to 4 carbon atoms, an alkoxy group containing 1 to 4 carbon atoms, a halogen, cyano-, nitro- or hydroxy radical or an amino group

wherein $R_1$ and $R_2$, which may be alike or different from each other each represent an alkyl group containing 1 to 4 carbon atoms; M represents a cation which is able to form water-soluble compounds of formula (I) selected from the group consisting of a proton, a cation derived from an alkali metal or an alkaline earth metal, ammonium, a group $N(R_3R_4R_5R_6)+$ wherein $R_3$, $R_4$, $R_5$ and $R_6$ each represent hydrogen or an alkyl group containing 1 to 4 carbon atoms and may be alike or different from each other, and a cation of any other metal, which is able to form watersoluble salts with benzosulfonic acids; $m_1$, $m_2$ and $m_3$ each represent a whole number from 0 to 5 which may be the same or different from each other, and $n_1$, $n_2$ and $n_3$ each represent a whole number from 0 to 3, which may be the same or different from each other, whereby at least one of these numbers $n_1$, $n_2$ and $n_3$ equals at least one and further comprising a compound selected from the group consisting of a transition metal, preferably palladium or a transition metal-containing compound, preferably a palladium containing compound.

Either before or after the reaction is completed, water is added to the reaction mixture, whereby an aqueous solution of the catalytic system is formed. When the reaction is finished, the reaction products can easily be separated from the reaction mixture and a major portion of the aqueous solution of the catalyst can be recovered for re-use.

The process is preferably used for telomerizing dienes, especially butadiene and derivatives thereof into diene derivatives containing the double amount of carbon atoms than the starting materials. Yet, it can also be used for tri- or tetramerization of dienes or for addition of a mobile hydrogen containing compound to a diene molecule.

The ratio between the amount of diene and a telomerizing compound is equivalent to at least one molecule of diene per ten atom of mobile hydrogen.

Further objects, features and advantages of the present invention will become apparent from the following detailed description of the invention and its preferred embodiment.

DETAILED DESCRIPTION OF THE INVENTION

Amongst the above-defined cations M, cations which are derived from lead, zinc, or tin, can be cited as examples of cations which are able to form water-soluble salts with benzosulfonic acids.

The process according to the present invention can be effected to either of the following two main embodiments.

According to the first embodiment, water is introduced before the telomerizing reaction is completed. According to the second embodiment, water is introduced only after the telomerizing reaction is completed.

Within the first embodiment, two different cases have to be distinguished. The first is related to the use of a mobile hydrogen-containing telomerizing compound which is sparingly soluble in water; the other is related to the use of a water-soluble mobile hydrogen-containing telomerizing compound (e.g., the use of methanol). If the mobile hydrogen-containing compound is not water-soluble, two phases will be present at the end of the reaction: an aqueous phase containing the catalyst and an organic phase containing the reaction products. In this case, for example, the separation is done simply by decantation or extraction. If the mobile hydrogen-containing compound is at least partially soluble in water, often only one single phase will be present at the end of the reaction. Then it is necessary to submit this reaction mixture to a distillation operation in order to eliminate the remaining unreacted amount of the mobile hydrogen-containing telomerizing compound, thereby obtaining a two-phase system of the kind described above.

The aqueous phase which is recovered after decantation or extraction can be directly recycled into the reaction. This permits one to carry out the process in a continuous operation.

Within the second embodiment, water is added only after the reaction is terminated, and a system identical to that obtained at the end of the reaction in the first embodiment is obtained. In this embodiment, of course, it will be necessary to eliminate the water again from the catalyst in any conventional manner before recycling the latter into the reaction. This can be done, for example, by adding a heavy solvent which permits to deplete the water.

In the first embodiment, the phosphines can be introduced into the reaction mixture in the form of an aqueous solution.

Preferred are such phosphine compounds of formula (I) wherein $Ar_1$, $Ar_2$ and $Ar_3$ each represent phenyl, $Y_1$, $Y_2$ and $Y_3$, which may be alike or different from each other, each represent an alkyl group containing 1 to 2 carbon atoms, an alkoxy group containing 1 to 2 carbon atoms or chlorine, M represent a proton, a cation derived from sodium, potassium, calcium or barium, ammonium, tetramethylammonium, tetraethylammonium, tetrapropylammonium or tetrabutylammonium; $m_1$, $m_2$ and $m_3$, which may be alike or different from each other, each represent a whole number between 0 and 3.

Among those phosphines of formula (I), the most preferred are the sodium, potassium, calcium, barium, ammonium, tetramethylammonium and tetraethylammonium salts of (sulfophenyl)diphenylphosphine, di(sulfophenyl) phenylphosphine and tri(sulfophenyl)-phosphine, wherein the $SO_3-$ groups preferably are situated in meta-position.

Further examples of phosphines of formula (I) which may be used according to the process of the present invention are alkali metal salts, alkaline earth metal salts, ammonium salts or quaternary ammonium salts of (m-sulfophenyl)diphenylphosphine, (p-sulfophenyl)diphenylphosphine, (m-sulfo-p-methylphenyl)di(p-methylphenyl)phosphine, (m-sulfo-p-methoxyphenyl)-di(p-methoxyphenyl)phosphine, (m-sulfo-p-chlorophenyl)di(p-chlorophenyl)phosphine, di(m-sulfophenyl)phenylphosphine, di(p-sulfophenyl)phenylphosphine, di(m-sulfo-p-methylphenyl) (p-methylphenyl)-phosphine, di(m-sulfo-p-methoxyphenyl (p-methoxyphenyl)phosphine, di(m-sulfo-p-chlorophenyl) (p-chlorophenyl)phosphine, tri(m-sulfophenyl)phosphine, tri(p-sulfophenyl)phosphine, tri(m-sulfo-p-methylphenyl)phosphine, tri(m-sulfo-p-methoxyphenyl)phosphine, tri(m-sulfo-p-chlorophenyl)phosphine, (o-sulfo-p-methylphenyl) (m-sulfo-p-methyl (m,m'-disulfo-p-methyl)phosphine, (m-sulfophenyl) (m-sulfo-p-chlorophenyl) (m,m'-disulfo-p-chlorophenyl)phosphine.

As stated before, a mixture of these phosphines, particularly a mixture of mono-, di-, or tri-metal-sulfonated phosphines can be used.

As a transition metal compound, preferably a palladium, nickel, platinum, cobalt or rhodium compound is used. Such compounds are used which are water-soluble or able to be dissolved under the reaction conditions. The group which is connected to the transition metal is not critical as long as these requirements are fulfilled.

These transition metals can also be used in the form of metals deposited onto an inert carrier, e.g., carbon black. Among the before-mentioned compounds, palladium compounds are most preferred. The following compounds are cited as non-limiting examples: compounds wherein the redox value of the palladium is other than zero, e.g., palladium acetate, carbonate, carboxylate, borate, bromide, chloride, citrate, hydroxides, iodide, nitrate, sulfate, arylsulfonates and alkylsulfonates, -acetylacetonate, bis(benzonitrile)palladium chloride, potassium tetrachloro palladate, and, $\pi$-allyl complexes of palladium, especially π-allyl palladium acetate or -chloride.

It is not necessary that the palladium compound as such be soluble in water. For example, the palladium acetate is not very soluble in water but dissolves very well in an aqueous phosphine solution.

Among the compounds wherein the redox value of the palladium equals zero, a large number of various complexes can be used. The latter may contain olefins, dienes, or cyano groups as a ligand. In particular, there can be used tetra(biphenyl)phosphine palladium (zero), bis(cyclo-octadiene-1,5) palladium (zero) or potassium tetracyano palladate. In this latter case, the compound may be dissolved in a non-water miscible solvent like toluene. An aqueous solution of a sulfonated phosphine extracts part of the palladium therefrom, whereby a yellow coloration develops in the decanted aqueous solution.

Finally, palladium metal deposited onto an inert support such as carbon black can also be used.

The amount of transition metal compounds, especially palladium compounds, which are used are chosen in such a range that the reaction solution contains between about $10^{-4}$ and about 1 gram atoms, preferably between about 0.005 and 0.5 gram atoms of elementary metal per liter.

The amount of phosphine compounds of formula (I), which is used within the reaction medium is chosen in the range that the reaction medium contains between about 1 to about 2,000, preferably between about 1 and 30 moles of phosphines per gram atom of elementary metal.

Even so, this is not absolutely necessary when palladium metal or one of the above-mentioned palladium compounds are used, a palladium reducing agent, preferably a palladium reducing agent which reacts with the palladium under the given reaction conditions, is added to the reaction medium. This reducing agent may be an organic or inorganic agent. The following agents are cited as non-limiting examples: sodium borohydride, powdered zinc, magnesium, potassium borohydride and other boron hydrides, preferably water-soluble boron hydrides.

It is advisable to add an amount of reducing agent which corresponds to between about 1 and about 10 redox equivalents. Nevertheless, the addition of lower amounts or higher amounts which correspond to more than 10 redox equivalents is not excluded.

Such a reducing agent may also be added if platinum or rhodium are used. If nickel or cobalt are used, the use of a reducing agent is necessary when their redox value is other than zero, but not imperative if the redox value equals zero. The same reducing agents which are used with palladium can be used.

The sulfonated phosphines which are used within the process of the present invention can be prepared by conventional methods. Thus, according to the teachings of H. Schindlebauer, *Monatsch. Chem.*, 96, pages 2051–2057 (1965), the sodium salt of (p-sulfophenyl)-diphenylphosphine can be prepared by reacting sodium p-chlorobenzene sulfonate with diphenylchlorophosphine in the presence of sodium or potassium. According to the method which is described in *J. Chem. Soc.*, pp. 276–288 (1958), and in the British Pat. No. 1,066,261, phenylphosphines of formula (I) can be prepared by using the method of sulfonating aromatic nuclei by means of oleum and then neutralizing the formed sulfonic groups by means of an appropriate basic derivative of one of the metals, which are represented by M in the formula (I). The crude sulfonated phosphines which are obtained may contain corresponding oxides of sulfonated phosphines mixed with them, yet the presence thereof does not interfere with performing the hydroxyanation process according to the present invention.

The process of the present invention is suited for telomerizing olefins, preferably aliphatic dienes, which contain 4 to 20, preferably 4 to 8, carbon atoms and may be substituted by lower alkyl groups. In particular, lower aliphatic conjugated dienes, such as, butadiene, isoprene, piperylene or dimethylbutadiene are treated according to the process of the present invention.

A telomerizing compound containing at least one mobile hydrogen atom is a compound which contains at least one reactive hydrogen atom. The following groups of compounds may be cited as examples of compounds containing reactive hydrogen atoms: water, alcohols, phenols, acids, amines, silanols or compounds containing a reactive methylene group.

Among the alcohols, the following may be cited as suitable examples: primary, aliphatic, saturated, branched or straight alcohols containing preferably 1 to 8 carbon atoms, such as, methanol, butanol and the like, unsaturated aliphatic alcohols containing preferably 3 to 8 carbon atoms, such as, allyl alcohol, saturated aliphatic or alicyclic secondary alcohols containing preferably 3 to 8 carbon atoms such as isopropanol or cyclohexanol, aromatic alcohols containing 7 to 12 carbon atoms, such as, benzyl alcohols, fluorinated aliphatic or aromatic alcohols, e.g., tertiary alcohols of the formula

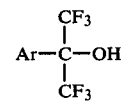

wherein Ar represents an aryl group containing 6 to 10 carbon atoms, preferably phenyl or benzyl, or alcohols of the formula $CF_3-(CF_2)_n-CH_2OH$, wherein n is an integer from 1 to 6, or polyols preferably containing 2 to 8 carbon atoms, e.g., glycol.

Among the phenols, unsubstituted phenols and phenols substituted by lower alkyl, lower alkoxy, or halogen are particularly suited. As examples, there may be cited phenol p-chlorophenol, o-methoxyphenol, dimethylphenols and cresols.

Among the acids, lower aliphatic and aromatic mono- or divalent acids, preferably containing less than 12 carbon atoms are particularly suited. As examples, there may be cited aliphatic monocarboxylic acids, such as acetic acid, aliphatic dicarboxylic acids, such as adipic acid, aromatic mono- or dicarboxylic acids, such as benzoic acid or o-phthalic acid.

Among the amines which can be used within the process according to the present invention, primary aliphatic or aromatic amines, e.g., lower alkyl amines, such as methylamine or aniline, secondary aliphatic or aromatic amines, e.g., di(lower alkyl) amines, such as diethylamine, lower alkyl anilines, such as methyl aniline, heterocyclic amines, preferably containing 5 or 6 ring members, e.g., piperidine or morpholine. Ammonia can also be used.

Among the compounds containing a reactive methylene group acetone derivatives, e.g., lower aliphatic or aromatic acyl or carboxyl derivatives of acetone are particularly suited. The following may be cited as examples: acetylacetone, benzoylacetone, ethyl acetoacetate. Also suited are nitro compounds e.g., nitro-methane.

By reacting 2 moles of diene, e.g., butadiene, with one mole of one of the various compounds HX', the following compounds are obtained:

$$\diagup\!\!\!\diagdown\!\!\!\diagup\!\!\!\diagdown\!\!\!\diagup\!\!\!\diagdown X, \quad \text{and} \quad \diagup\!\!\!\diagdown\!\!\!\diagup\!\!\!\diagdown\!\!\!\diagup\!\!\!\diagdown^{X'}$$

wherein X' is:

$$-OH, -OR, -O\phi, -NR_2, -OCOR, -\underset{\underset{Y}{\overset{\overset{C=O}{|}}{CH,}}}{\overset{\overset{2}{|}}{CH,}} -CH_2NO_2 \text{ or } -OSiR_3$$

wherein 2 is alkyl or aryl and Y is alkyl, aryl or alkoxy.

By reacting one mole of butadiene with one mole of a compound HX'', wherein X'' is $-O\phi'-OCOCH_3$ or $NR_2$, the following compounds are obtained:

$$\diagup\!\!\!\diagdown\!\!\!\diagup\!\!\!\diagdown\!\!\!\diagup\!\!\!\diagdown X'', \quad \text{and} \quad \diagup\!\!\!\diagdown\!\!\!\diagup\!\!\!\diagdown\!\!\!\diagup\!\!\!\diagdown^{X''}$$

In the case that the mobile hydrogen-containing compounds include more than one mobile hydrogen atom per molecule, a replacement of all the mobile hydrogen atoms can be obtained. Thus, starting from butadiene and an amine $RNH_2$ dioctadienyl alkyl- or aryl amines of the formula $$(\diagup\!\!\!\diagdown\!\!\!\diagup\!\!\!\diagdown\!\!\!\diagup\!\!\!\diagdown)_2NR$$

are obtained.

According to the present invention, the following compounds are prepared:
1-methoxy-2,6-dimethyloctadiene-2,7 starting from 1-isoprene and methanol
octadiene-2,7-ol-1 starting from butadiene and water
1-acetocyoctadiene-2,7 starting from butadiene and acetic acid
1-phenoxyoctadiene-2,7 starting from butadiene and phenol
N,N-diethylamino-1-octadiene-2,7 and N,N-diethylamino-1-butene-2 starting from butadiene and diethylamine
N-octadienyl-2,7-morpholine starting from butadiene and morpholine.

The compounds which are obtained according to the present invention are useful as intermediates for the synthesis of plasticizers, plastic materials, perfumes, pharmaceuticals and galvano plastics.

The process according to the present invention may be effected in the presence of further additives. Suitable additives are bases, such as hydroxides of alkali metals, alkaline earth metals, tertiary aliphatic or aromatic amines, phenolates, or solutions corresponding to mixtures of the beforementioned bases and acids, such as, for example, mineral acids of elements of the Group IIIA, such as, boric acid, acids of elements of the Group IVA, such as, carbonic acid, acids of elements of the Group VA, such as, phosphoric acid and acids of tri or five valent phosphorus, or arsenic acid, acids of elements of the Group VIA, such as, sulfuric acid, sulfurous acid or alkylsulfonic acid, acids of elements of the Group VIIA such as hydrofluoric acid, hydrochloric acid, hydrobromic acid, or hydroiodic acid, organic acids such as trifluoromethane sulfonic acid, trifluoroacetic acid, aryl- or alkylsulfonic acids, carboxylic acids such as, acetic acid and weak acids like phenol.

For each mobile hydrogen containing compound, the person skilled in the art can choose the appropriate combination of the above-mentioned additives in order to achieve the best reaction speed and to facilitate the recycling.

Due to its low reactivity, water will not chemically interfere as a reactant in the case where it is used as a solvent for the catalyst. It has been found that when water is used as a mobile hydrogen-containing reactant, the addition of certain water-soluble compounds significantly increases the reaction speed. Among these compounds are alkaline electrolytes, alkali carbonates and -bicarbonates, such as, sodium carbonate and -bicarbonate, sodium silicates and alkaline salts of phosphorous phosphoric and arsenic acids.

It may be advisable to add to the reaction mixture an organic solvent which is inert towards the various components of the reaction mixture. There can be used a solvent which is immiscible with water or a solvent which is miscible with water. In the latter case, the solubility of, e.g., the butadiene in water increases and the reaction speed can be increased. Solvents which are immiscible with water provide for a better decantation.

The following are cited as examples for water miscible solvents: acetone, acetonitrile, dimethylether or diethylene glycol, dimethoxyethane, dioxane, tert. butanol, dimethyl acetamide, n-methyl pyrolidone and ethylene carbonate, dimethoxyethane, and as examples of immiscible solvents, benzene, benzonitrile, acetophenone, isopropyl ether, octane, methylethylacetone and propionitrile can be mentioned.

The temperature at which the reaction is performed may vary within wide ranges. Moderate temperatures between −20° to 200° C., preferably temperatures between about 20° and about 125° C., are particularly suitable.

According to an embodiment of the process of this invention, an appropriate reaction vessel, which has been purged by means of an inert gas (nitrogen or argon) is charged either with an aqueous catalytic solution which was prepared before or with the various components: a phosphine, water, the transition metal compound optionally together with a reducing agent, an additive, and an organic solvent. The reaction vessel is brought to the reaction temperature before or after the mobile hydrogen-containing compound is introduced, which itself may be introduced before, after or simultaneously with the diene.

After stopping the reaction, the mixture is cooled to room temperature. The content of the reaction vessel is drawn from the vessel, and afterwards, the reaction product has only to be recovered by subsequent decantation or eventually by extraction by means of appropriate solvents such as, e.g., the water immiscible solvents which were cited above.

The remaining aqueous solution may be recycled into the reaction vessel for catalyzing a new reaction. The aqueous solution may also stay in the reaction vessel when the organic compounds are drawn from it.

Another embodiment of the process according to the present invention comprises carrying out the above operation but introducing the water only after the reaction as such has stopped. In this case, before recycling the catalyst, the water has to be eliminated again by any convenient means.

It was found that the process according to the present invention allows to obtain yields which depending on the respective reaction can be as high as 95%.

The following examples are intended only to further illustrate the invention without limiting it.

EXAMPLE 1

Into a 500 ml stainless steel autoclave which was equipped with a knock-type agitation system, the following were introduced:
40 g of a solution containing:
  0.0178 g (0.1 m mole) of palladium chloride and
  0.124 g (0.3 m mole) of the mono sodium salt of (m-sulfophenyl)diphenylphosphine dihydrate content in trivalent phosphorus 95% of the theoretical amount) in methanol.
40 g of additional methanol
0.100 g (1.8 m mole) of potash
0.030 g (1 m mole) of sodium borohydride The autoclave was purged for 30 minutes with argon, then 25 g of butadiene were introduced. The autoclave was than agitated for 21 hours at 30° C. Then also at 30° C., 4 g of butadiene were degassed. The reaction mixture was transferred into a distillation apparatus. It was composed of one yellow limpid phase. Butadiene and methanol were removed by distillation at a pressure of 100 mm mercury by heating the flask up to 33° C. and adding water. The concentrated reaction mixture contained two phases:
7.9 g of an aqueous phase of yellow color containing the catalytic system
a colorless organic phase comprising mainly the methoxy octadienes.

According to chromatographical analysis, the following results were obtained by the above procedure:
percentage of conversion of the butadiene: 56%
yields per amount of used up butadiene:

| 1-MOD: | 95% | MOD = | methoxyoctadiene |
| 3-MOD: | 4% | | |
| C$_8$: | traces less than 1% | C$_8$ = | other hydrocarbon compounds containing 8 carbon atoms per molecule |

The catalytic system was in the aqueous phase.

EXAMPLE 2

Into a 500 ml stainless steel autoclave which was equipped with a knock-type agitation system, the following were introduced:
0.224 g (1 m mole) of palladium acetate
0.464 g (4 m mole) of sodium phenolate
2 g (3.9 m mole) of the mono sodium salt of (m-sulfophenyl) diphenylphosphine dihydrate (content in trivalent phosphorus 80% of the theoretical amount)
15 ml of water
78.6 g of methanol This was purged for 30 minutes with argon, then 70 g of butadiene was introduced. The autoclave was then agitated at 95° C. for 18 hours and then cooled to 50° C. in order to eliminate the unreacted butadiene (less than 2 g). Then at 35° C. and under argon, the content of the autoclave was transfered into a conical distillation apparatus through which argon was passed. The reaction mixture comprised two phases. Methanol was removed by distillation. The distillation was carried out at atmospheric pressure by heating the boiler to 101° C., whereby the temperature at the top of the column was 90.5° C. During the distillation, 10 ml of water were added in order to obtain an aqueous phase the volume of which was between about 15 and 30 ml. This aqueous phase, which contained the catalyst, was recycled into the autoclave under argon. The supernatant organic phase, the weight of which was 75.6 g, comprised mainly methoxyoctadienes.

According to chromatographical analysis, the following results were obtained by the above procedure:
percentage of conversion of the butadiene: >95%
yields per amount of used up butadiene:
  1-MOD: 78%
  3-MOD 7%
  C$_8$: 11%

The remainder to 100% was comprised of mainly oligomers and telomers.

EXAMPLE 3

Into a 125 ml stainless steel autoclave, which was equipped with a knock-type agitation system, the following were introduced:
0.039 g of palladium acetate
0.958 g of the tetramethylammonium salt of tri(m-sulfophenyl) phosphine (purity 60%)
8.5 g of methanol.

The autoclave was purged for 30 minutes with argon then 10.5 g of butadiene were introduced. The autoclave was then agitated for 16 hours at 95° C. The autoclave was cooled, then the reaction products were distilled at a pressure of 0.1 mm mercury by heating the autoclave to 80° C.

With the catalytic system which remained in the autoclave the same operation was repeated three times using the following reactants:
2nd operation—25 g of butadiene, 23 g of methanol;
3rd operation—21 g of butadiene, 24 g of methanol;
4th operation—24 g of butadiene, 25 g of methanol.

According to the analytical data, the percentage of conversion of the butadiene was 100% and it was transformed into:
dimer hydrocarbons 20%, mainly octatriene-1,3,7.
1-MOD: 59%; 3-MOD: 10%; heavy products: 11%.

The catalytic system was separated from the heavy products by adding water and decanting.

EXAMPLES 4, 5 and 6

Into a 125 ml stainless steel autoclave which was equipped with a knock-type agitation system, tests with different phosphines were carried out. After introducing the reactants and the catalytic system and allowing the reaction to take place for 18 hours at 95° C., the separation of the catalytic system was effected by adding water. The results are shown in the Table below:

Example 4: tetraethylammonium salt of tri(m-sulfophenyl) phosphine (purity: 60% determined as trivalent phosphorus)

Example 5: monosodium salt of (m-sulfophenyl)-diphenyl phosphine dehydrate (purity 85%).

Example 6: disodium salt of di(m-sulfophenyl)phenyl phosphine (purity 100%, determined as trivalent phosphorus). Amound of methanol: 20 ml, amount of butadiene: 20 ml.

| Ex. | Weight of the ligand (g) | Pd(oAc)$_2$ mg | Conversion of butadiene | Selectivity % 1-MOD | 3-MOD | C$_8$ |
|-----|----|----|-----|----|----|----|
| 4 | 0.96 | 39 | 100 | 70 | 14 | 11 |
| 5 | 0.32 | 34 | 90 | 83 | 7 | 9 |
| 6 | 0.35 | 38 | 83 | 78 | 8 | 11 |

With the mono sodium salt of (p-sulfophenyl)diphenylphosphine prepared according to Schindlbauer, essentially the same results were obtained.

EXAMPLE 7

Into a 125 ml stainless steel autoclave which is equipped with a knock-type agitation system, the following were introduced:
0.135 g of palladium acetate (0.6 m mole)
1.61 g of trisodium salt of tri(m-sulfophenyl)phosphine (purity 90%) (2.4 m mole) (TPPS)
10.8 ml of water
1.38 g of potassium carbonate (10 m moles), that is a concentration of one mole/l water.

The autoclave was purged for 30 minutes with argon, then 18 g of butadiene were added. Then the autoclave was agitated for 3 hours at 80° C., then cooled to 60° C. for eliminating the major portion of unreacted butadiene by degassing. After cooling to 20° C., and opening the autoclave, a reaction mixture comprising two layers were removed into a decantor. The two layers were:
an aqueous layer (10.6 g) containing the catalytic system
an organic layer (11.8 g) containing the following components according to chromatographical analysis:
10% of C$_8$ - hydrocarbons mainly octatriene-1,3,7
63% of octadiene-2,7-ol-1 (=ol-1)
21% of octadiene-1,7-ol-3 (=ol-3)

The remainder of 100% comprises mainly butadiene and heavier products than octadienols. The aqueous layer is used for carrying out further new operations.

EXAMPLES 8–16

According to the method described in Example 7, a certain number of tests were carried out adding different co-catalysts to the water. The results demonstrate well the necessity of finding out the appropriate combinations of acids and bases for each telomerization reaction in order to obtain the best results. For example, palladium in an aqueous solution of sulfonated phosphine is not very active in catalyzing the addition of water; on the contrary, adding carbonate, bicarbonate, phosphate, phosphites, silicates or arsenates, permits to markedly accelerate the reaction.

TABLE

| | Charges | | | | Results per amount of butadiene | | | | Level of catalysis [1] |
|---|---|---|---|---|---|---|---|---|---|
| Examples | Butadiene | Palladium acetate | Phosphine | Additives | Percentages of conversion | C$_8$ | Yields 1-ol | Yields 3-ol | |
| 8 | 22 g | 0.135 g 0.6 m mole | 1.6 g 2.4 m mole | | 1.3% | 66% | 28% | 6% | 4.5 |
| 9 | 18 g | 0.135 g 0.6 m mole | 1.6 g 2.4 m mole | K$_2$CO$_3$ 1.38 g 1 mol/l | 71% | 10% | 63% | 21% | 202 |
| 10 | 19 g | 0.135 g 0.6 m mole | 1.22 g 1.8 m mole | K$_2$CO$_3$ 1.38 g 1 mol/l | 76% | 12% | 64% | 20% | 229 |
| 11 | 16.2 g | 0.135 g 0.6 m mole | 1.22 g 1.8 m mole | KH CO$_3$ 1 g 1 mol/l | 35% | 9% | 78% | 13% | 90 |
| 12 | 20 g | 0.0337 g 0.15 m mole | 0.4 g 0.6 m mole | K$_2$ CO$_3$ 1 mol/l | 13% | 6.5% | 71% | 22% | 162.5 |
| 13 | 23 g | 0.0337 g 0.15 m mole | 0.4 g 0.6 m mole | H$_3$PO$_4$ 1 mol/l NaOH 2.5 mol/l | 9% | 25% | 62% | 12.3% | 129 |
| 14 | 28 g | 0.0337 g 0.15 m mole | 0.4 g 0.6 m mole | H$_3$PO$_3$ 1 mol/l NaOH 2.5 mol/l | 14.5% | 16.9% | 58% | 21% | 254 |
| 15 | 13 g | 0.0337 g 0.15 m mol | 0.4 g 0.6 m mole | Na$_2$H AsO$_4$ 1 mol/l NaOH 0.5 mol/l | 8% | 24% | 56% | 15% | 65 |
| 16 | 18 g | 0.0337 g 0.15 m mole | 0.4 g 0.6 m mole | Sodium Silicate[2] | 24% | 16% | 68% | 15% | 270 |

[1] The level of catalysis was determined as the ratio between the weight of butadiene which had reacted and the weight of the palladium which was applied.
[2] 5 ml of an aqueous solution having a density of 1.3 (sold by Societe PROLABO)

EXAMPLES 17 AND 18

Into a 125 ml stainless steel autoclave purged with argon and equipped with a knock-type agitation system, the following were introduced:

| | Water | TPPS | Salt | Sodium Phenolate | Phenol | Butadiene |
|---|---|---|---|---|---|---|
| Ex. 17 | 10.8 cm3 | 2.4 m mole | Pd(oAc)$_2$ 0.6 m mole | 1.25 g 1 mole/l | 18.8 g | 23 g |
| Ex. | 10.8 | 1.36 | PtCl$_2$ | 1.25 g | 18.8 g | 23 g |

| | Water | TPPS | Salt | Sodium Phenolate | Phenol | Butadiene |
|---|---|---|---|---|---|---|
| 18 | cm3 | m mole | 0.45 m mole | 1 mole/1 | | |

The autoclave was then agitated for 3 hours at 80° C. then cooled to 60° C. in order to eliminate the major portion of the unreacted butadiene. After cooling to 20° C. and opening of the autoclave, the reaction mixture comprising two layers were recovered into a decantor. The upper phase contained the organic products, the below aqueous phase contained the catalyst and sodium phenolate. According to the analysis, the percentage of conversion and the yields were as follows:

| | Ex. 17 | Ex. 18 |
|---|---|---|
| Percentage conversion of butadiene | 90% | 40% |
| Yield in hydrocarbons C₈ | 18% | 5.5% |
| Yield in 1-phenoxybutene-2 | 1% | 18.5% |
| Yield in 3-phenoxybutene-1 | 0.8% | 18.5% |
| Yield in 3-phenoxyoctadiene-1,7 | 21% | 4.46% |
| Yield in 1-phenoxyoctadiene-2,7 | 56% | 46.2% |

EXAMPLE 19

Into a 125 ml stainless steel autoclave purged with argon and equipped with a knock-type agitation system, the following were charged:
10.8 g water
1.83 g trisodium salt of tri(m-sulfophenyl)phosphine (purity 90%)
0.135 g of palladium acetate
14.6 g of diethylamine
19 g of butadiene.

The autoclave was then agitated during 3 hours at 85° C. then cooled to 60° C. in order to eliminate a portion of the unreacted butadiene. The reaction mixture formed two distinct immiscible layers which were decanted. The aqueous layer containing the catalyst weighed 12.5 g. The colorless organic layer weighed 29 g, it contained:
13.5% of butadiene
46.5% of 1-(N,N-diethylamino)butene-2
40% of 1-(N,N-diethylamino)octadiene-2,7
0.6% of 3-(N,N-diethylamino)octadiene-1,7

EXAMPLE 20

Into a 125 ml stainless steel autoclave purged with argon and equipped with a knock-type agitation system, the following were introduced:
12 g of acetic acid
17.8 g of dimethylamino-2-ethanol
0.33 g of tetraethylammonium salt of tri(m-sulfophenyl) phosphine (purity 90%)
0.050 g of palladium acetylacetonate
10.5 g of butadiene The autoclave was then agitated for two hours at 90° C., then cooled to 60° C. in order to eliminate a portion of the unreacted butadiene. The reaction mixture was distilled. The catalytic system was separated from the heavy products by adding water and decanting. According to the analysis of the distillates, the percentage of conversion of the butadiene was 94%, namely 56% of 1-acetoxyoctadiene-2,7 and 36% of dimer hydrocarbons that is octatriene-1,3,7.

EXAMPLE 21

Into a conical 250 ml flask purged with argon, the following were introduced:
80.8 g of methanol
0.330 g of mono sodium salt of (m-sulfophenyl)diphenylphosphine, (purity 97%)
0.045 g of palladium acetate
0.6 g of potash
0.035 g of sodium borohydride
28 g of isoprene.

The homogeneous mixture was agitated for 68 hours at 45° C. The mixture was cooled and 60 ml of water and 0.33 g of phosphine were added, then methanol and isoprene were removed from the boiler by heating them to 36° C. under a pressure of 100 mm of mercury. The supernatant organic colorless phase weighed 21 g and contained 70% of methoxy-1-dimethyl-2,6-octadiene-2,7, the remainder to 100% consisting of dimer hydrocarbons, as isomer and heavier products. The aqueous phase contained the catalytic system.

EXAMPLE 22

Into a 125 ml stainless steel autoclave purged with argon and equipped with a knock-type agitation system, the following were introduced:
20 ml of methanol
0.45 g of sodium salt of (m-sulfophenyl)bis(phenyl)-phosphine, (purity 97%)
0.5 g of palladium on carbon black 10%
19 g of butadiene The mixture was then agitated during 3 hours at 85° C., then cooled to 60° C. in order to eliminate a portion of the unreacted butadiene. The reaction mixture was filtered in order to eliminate the carbon black therein. The organic phase contained unreacted methanol and:
15 g of methoxy-1-octadiene-2,7
0.75 g of methoxy-3-octadiene-1,7
0.75 g of a dimer of butadiene The catalyst can be separated from the reaction mixture as described in Example 2.

EXAMPLE 23

Into a 10 ml glass tube, the following were introduced under argon atmosphere:
0.679 g of mono sodium salt of (m-sulfophenyl)diphenylphosphine, (purity 97%)
5 ml of ethanol.

The tube was cooled to −78° C. and then were introduced:
0.107 g of anhydrous nickel chloride
0.27 g of butadiene
0.123 g of sodium borohydride The glass tube was then isolated and closed by means of a Bakelite screw closure which comprised a rubber insert which allowed the injection of liquids by means of a syringe.

The mixture was allowed to warm up to −40° C. 1.36 g of butadiene and 0.8 ml of morpholine were added. The reaction mixture was reheated to 20° C. and maintained at 20° C. for 1 hour and 30 minutes. According to chromatographical analysis, the percentage of conversion of morpholine was above 95% with a yield of 90% of N-octadienylmorpholine. The ethanol was removed by distillation. The catalyst was separated from the reaction products by adding water.

PREPARATION OF THE PHOSPHINES WHICH WERE USED IN THE EXAMPLES (1) Preparation of the sodium salt of (metasulfophenyl) diphenylphosphine.

This phosphine was prepared according to the preparation method, which is described by S. Ahrland, J. Chatt, N. R. Davies, A. A. Williams, *Journal of Chemical Society*, 276–288 (1958).

(2) Preparation of the sodium salt of (p-sulfophenyl) diphenylphosphine.

This phosphine was prepared according to the preparation method described by H. Schindlbauer, *Monatsch. Chem.*, 96, pp. 2051–2057 (1965) by reacting sodium p-chlorobenzene sulfonate with diphenylchlorophosphine in the presence of sodium.

(3) Preparation of the sodium salt of tri-(metasulfophenyl)phosphine.

Into a 2 liter balloon flask which was equipped with a central stirring system, a thermometer and an ascendent cooler and which was cooled from the outside by an ice water bath, there was introduced a liter of oleum containing 20% by weight of sulfuric anhydride, then the flask was purged with argon. The stirring was started, subsequently 100 g of triphenylphosphine were introduced within 2 hours thereby keeping the temperature between 20° and 40° C. When the addition was finished, stirring of the mixture was continued at the above temperature during 15 to 25 hours. The reaction was then cooled to 10° C. and was carefully poured into a 10 liter balloon flask which contains 2 liters of water which was cooled to 0° C. 1,500 g of sodium hydroxide pastils were added to the reaction mixture, whereby the temperature of the reaction medium was maintained at below 20° C. The resulting solution was allowed to stand for several hours at room temperature, at about 20° C.

At the end of this period, the precipitated sodium salts were recovered by filtration and washed twice with 1,500 ml of ice water each. The combined filtrates and washing waters were concentrated to a total volume of 1,500 ml by heating at reduced pressure.

The precipitate which was obtained at the end of the concentrating operation was filtered and washed three time with 300 ml ice water each. The combined filtrate and washing waters were concentrated to a volume of 500 ml by heating under reduced pressure.

To the mixture remaining from the above concentration step, 500 ml of methanol were added, then the forming precipitate was filtered and washed with 500 ml of a mixture of methanol/water 50/50. The combined filtrate and washing solutions were then concentrated to a volume of 200 ml, then 1,000 ml of methanol were added. The precipitate which was formed was filtered, then washed six times with 1,000 ml of methanol heated to 60° C. The molten liquors and washing solution were combined and evaporated to dryness. The evaporation residue was introduced into 500 ml of absolute ethanol. The resulting solution was filtered and the solids on the filter were washed with 20 ml of ethanol and then dried at 25° C. under reduced pressure (0.1 mm mercury) during 30 hours. 172 g of a white solid remain.

The results of analyzing the product by elementary analysis (determination of the content in C, H, S, P) by infra red spectroscopy by nuclear magnetic resonance of hydrogen and phosphorus and by chemical determination of the trivalent phosphorus (iodometric determination), and the sulfonated groups by ion exchange indicated that the product was a mixture of tri sodium salts of tri(metasulfophenyl)phosphine and of tri(metasulfophenyl)phosphine oxide.

The composition of the mixture of salts may vary according to the temperature and the reaction time of the sulfonation. When the addition of the triphenylphosphine is effected at a temperature of about 30° C., and agitating of the mixture is continued at this temperature for about 20 hours, a mixture is recovered wherein 80% by weight of the salts in the solution are sodium salts of tri(metasulfophenyl)phosphine and 20% by weight are sodium salts of tri(metasulfophenyl)phosphine oxide. When working at 40° C. for 24 hours, the obtained mixture of salts contains 60% by weight of the sodium salt of the tri(metasulfophenyl)phosphine.

By carrying out the reaction at 18°–20° C. during 48 hours a product having a purity of above 95% is obtained.

(4) Preparation of an ammonium salt of tri(metasulfophenyl)phosphine.

A suitable amount of the sodium salt of tri(m-sulfophenyl)phosphine which was prepared as described above, was dissolved in water and the solution was passed through a column which contained an excess (about 4 times the theoretical amount) of a strongly acid ion exchange resin (sulfonic acid) which is known under the tradename Amberlite IR 120H, finally was eluated with water. The resulting acid solution was neutralized with tetraethylammonium hydroxide and then was evaporated to dryness under reduced pressure.

All triphenylphosphine salts can be prepared according to the same procedure.

(5) Preparation of the sodium salt of di(Metasulfophenyl)phosphine.

This phosphine is obtained by the following reaction. Into an 0.5 liter balloon flask which was equipped with a central stirring system, a thermometer and an ascendent cooler and which was cooled from the outside by an ice water bath, there were introduced 100 ml of oleum containing 20% by weight of sulfuric anhydride, then the flask was purged with argon. The stirring was started, subsequently 10 g of triphenylphosphine were introduced thereby keeping the temperature at 25° C. Stirring of the mixture was continued at this temperature during 17 hours. The reaction mixture was poured into a flask which contained 1,000 g of ice then the mixture was neutralized by means of 400 ml of an aqueous 10 N sodium hydroxide solution.

The precipitated salts were filtered and then dried to constant weight. 18 g of a solid was obtained and was introduced into 65 ml of water, which was heated to boiling. The insoluble particles were separated by hot filtration and the filtrate was left to cool to 20° C. The precipitated solid was separated by filtration, washed with 10 ml of cold water, then dried at 25° C. under a pressure of 0.1 mm mercury during 30 hours. Thus, 8 g of the disodium salt of pure di(m-sulfophenyl)phosphine were recovered.

EXAMPLE 24

A test was carried out analogous to Example 12, but replacing the potassium carbonate by 1.64 g of sodium phenyl sulphinate (i.e., a concentration of 1 mole per liter). The degree of conversion of the butadiene was 55%. The supernatant organic phase contained hydrocarbon dimers of butadiene (yield 9.7%), of 2-trans,7-octadiene-1-ol (yield 62%) and of 1,7-octadiene-3-ol (yield 16%).

EXAMPLE 25

In a 125 cm³ stainless steel autoclave equipped with a shaker were introduced:
0.040 g of platinum chloride (PtCl₂)
0.38 g of the trisodium salt of tri(meta-sulphophenyl)-phosphine (purity 95%)
10.8 cm³ of water
13.8 g of diethylamine.

The autoclave was purged for 30 minutes with argon and then 18 g of butadiene were introduced. The autoclave was then agitated for 3 hours at 80° C. and then cooled to 60° C. in order to remove the bulk of the butadiene which had not reacted, by degassing. After cooling to 20° C. and opening the autoclave, a reaction mixture, which consisted of the following two layers, was collected in a decanter:
an aqueous layer (9.1 g) containing the catalytic system
an organic layer (15.6 g) containing part of the reactants which had not reacted and 3.99 g of 1-diethylamino-2-trans-butene as the sole reaction product.

EXAMPLE 26

Following the procedure of Example 25, an experiment was carried out with the following materials:
0.036 g of [RhCl(cycloocta-1,5-diene)]₂
0.114 g of trisodium salt of tri(m-sulfophenyl)phosphine (purity 95%)
10.8 cm³ of water
14.8 g of diethylamine, and
19 g of butadiene The degree of conversion of the butadiene was about 10%. It had been converted into 1-diethylamino-2-trans-butene (23%) and 1-N-diethylamino-2-trans,7-octadiene.

EXAMPLE 27

When a taxogen, such as diethylamine is used, the addition of acid can effect the selectivity. For example, by following the procedure of Example 19, but adding 0.024 mole of sulphuric acid a reaction mixture was obtained containing, by mole:
13.9% of C₈ hydrocarbon
64.4% of 1-N-diethylamino-2,7-octadiene
13.9% of octadienol.

The absence of 1-diethylamino-2-trans-butene is noted.

EXAMPLE 28

The following constituents were introduced into a 125 cm³ stainless steel autoclave fitted with a shaker:
0.107 g of platinum chloride (PtCl₂)
0.815 g of trisodium salt of tri(m-sulfophenyl)phosphine (purity 95%)
10.8 g of water
14.6 g of diethylamine
20 g of isoprene.

The autoclave was then agitated for 20 hours at 80° C. After cooling, 32.2 g of an organic phase were decanted. The degree of conversion of the amine was about 93%, it had been converted into:
1-N-diethylamino-2-methyl-2-trans-butene (24%).

1-N-diethylamino-3-methyl-2-trans-butene (72%).

The process according to the present invention is preferably suited for reacting a sufficient amount of a compound of formula (II)

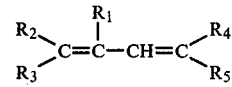

containing 4 to about 20 carbon atoms,
wherein at least one of the substituents $R_1$, $R_2$, $R_3$, $R_4$ and $R_5$ is hydrogen and the remaining substituents $R_1$, $R_2$, $R_3$, $R_4$ and $R_5$ are the same or different and each represent hydrogen, alkyl having 1 to 5 carbon atoms or alkenyl having 3 to 5 carbon atoms, with a telomerizing compound HOR, wherein R represents hydrogen, alkyl having 1 to about 20 carbon atoms, alkenyl having 3 to about 20 carbon atoms, aryl having 6 to about 20 carbon atoms, or an

group, wherein $R_6$ and $R_7$ are the same or different and each are hydrogen, alkyl having 1 to 20 carbon atoms or alkenyl having 3 to 20 carbon atoms or $R_6$ and $R_7$ together with the nitrogen atom form a 5- or 6-membered heterocyclus to form a reaction product containing a major portion of dimer derivatives of the compound of formula (II).

While the invention has now been described in terms of various preferred embodiments, and exemplified with respect thereto, the skilled artisan will appreciate that various substitutions, changes, omissions, and modifications may be made without departing from the spirit thereof. Accordingly, it is intended that the scope of the invention be limited solely by that of the following claims.

What is claimed is:

1. A process for telomerizing dienes which comprises the step of reacting a diene with a non-aqueous telomerizing compound containing at least one mobile hydrogen atom, said telomerizing agent being selected from the group consisting of an alcohol and a phenol, in the presence of a water-soluble catalytic system comprising at least one water-soluble phosphine having the following formula (I):

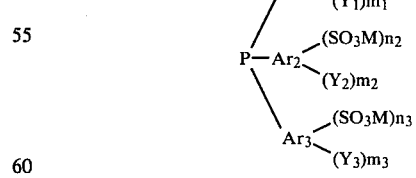

wherein $Ar_1$, $Ar_2$ and $Ar_3$ each represent an aryl group having from 6 to 10 carbon atoms, which may be alike or different from each other; $Y_1$, $Y_2$ and $Y_3$, which may be alike or different from each other each represent an alkyl group containing 1 to 4 carbon atoms, an alkoxy group containing 1 to 4 carbon atoms, a halogen, cyano-, nitro-, or hydroxy radical or an amino group

wherein $R_1$ and $R_2$, which may be alike or different from each other each represent an alkyl group containing 1 to 4 carbon atoms; M represents a cation which is able to form water-soluble compounds of formula (I) selected from the group consisting of a proton, a cation derived from an alkali metal or an alkaline earth metal, ammonium, a group $N(R_3R_4R_5R_6)+$, wherein $R_3$, $R_4$, $R_5$ and $R_6$ each represent hydrogen or an alkyl group containing 1 to 4 carbon atoms and may be alike or different from each other, and a cation of any other metal, which is able to form water-soluble salts with benzosulfonic acids; $m_1$, $m_2$ and $m_3$ each represent a whole number from 0 to 5 which may be the same or different from each other and $n_1$, $n_2$ and $n_3$ each represent a whole number from 0 to 3, which may be the same or different from each other, whereby at least one of these numbers $n_1$, $n_2$ and $n_3$ equals at least one and further comprising a compound selected from the group consisting of a transition metal or a transition metal-containing compound which is water soluble or able to be dissolved under conditions of the reaction 2. The process as defined in claim 1, wherein the diene is a diene having 4 to about 20 carbon atoms.

3. The process as defined in claim 1, wherein the ratio between the amount of diene and of telomerizing compound is equivalent to at least one molecule of diene per ten atom of mobile hydrogen.

4. The process as defined in claim 1, further comprising the step of introducing water into the reaction mixture thereby forming an aqueous solution of said catalytic system.

5. The process as defined in claim 4, wherein the water is introduced after the reaction is terminated.

6. The process as defined in claim 1, wherein $Ar_1$, $Ar_2$ and $Ar_3$ each represent phenyl.

7. The process as defined in claim 1, wherein $Y_1$, $Y_2$ and $Y_3$, which may be alike or different from each other, each represent an alkyl group containing 1 to 2 carbon atoms, an alkoxy group containing 1 to 2 carbon atoms or chlorine.

8. The process as defined in claim 1, wherein M represents a proton, a cation derived from sodium, potassium, calcium or barium, ammonium, tetramethyl ammonium, tetraethyl ammonium, tetrapropyl ammonium or tetrabutyl ammonium.

9. The process as defined in claim 1, wherein $m_1$, $m_2$ and $m_3$, which may be alike or different from each other each represent a whole number between 0 and 3.

10. The process as defined in claim 1, wherein $Ar_1$, $Ar_2$ and $Ar_3$ each represent phenyl, $Y_1$, $Y_2$ and $Y_3$, which may be alike or different from each other, each represent an alkyl group containing 1 to 2 carbon atoms, an alkoxy group containing 1 to 2 carbon atoms or chlorine, M represents a cation of the group consisting of a proton, a cation derived from sodium, potassium, calcium or barium, ammonium, tetramethyl ammonium, tetraethyl ammonium, tetrapropyl ammonium or tetrabutyl ammonium and $m_1$, $m_2$ and $m_3$, which may be alike or different from each other each represent a whole number between 0 and 3.

11. The process as defined in claim 1, wherein $Ar_1$, $Ar_2$ and $Ar_3$ each represent phenyl, $n_1$ represents 1, $n_2$, $n_3$, $m_1$, $m_2$ and $m_3$ each represent zero, and M represents a proton, a cation derived from sodium, potassium, calcium or barium, ammonium, tetramethyl ammonium or tetraethyl ammonium.

12. The process as defined in claim 1, wherein $Ar_1$, $Ar_2$ and $Ar_3$ each represent phenyl, $n_1$ and $n_2$ each represent 1, $m_1$, $m_2$, $m_3$ and $n_3$ each represent zero, and M represents a proton, a cation derived from sodium, potassium, calcium or barium, ammonium, tetramethyl ammonium or tetraethyl ammonium.

13. The process as defined in claim 1, wherein $Ar_1$, $Ar_2$ and $Ar_3$ each represent phenyl, $n_1$, $n_2$ and $n_3$ each represent 1, $m_1$, $m_2$ and $m_3$ each represent zero, and M represents a proton, a cation derived from sodium, potassium, calcium or barium, ammonium, tetramethyl ammonium or tetraethyl ammonium.

14. The process as defined in claim 9, wherein at least one of the sulfo groups which are present therein in each of the phenyl groups $Ar_1$, $Ar_2$ or $Ar_3$ is situated in m-position.

15. The process as defined in claim 1, wherein the transition metal is a metal from the group of palladium, nickel, platinum, cobalt, and rhodium.

16. The process as defined in claim 15, wherein the transition compound is palladium.

17. The process as defined in claim 16, wherein the palladium is deposited onto an inert carrier material.

18. The process as defined in claim 15, wherein at least part of the transition metal is zero valent.

19. The process as defined in claim 1, wherein the transition metal-containing compound is a compound containing palladium, nickel, platinum, cobalt or rhodium.

20. The process as defined in claim 19, wherein the transition metal-containing compound is a palladium compound.

21. The process as defined in claim 20, wherein the palladium compound is a compound from the group of palladium-acetate, -carboxylate, -carbonate, -borate, -bromide, -chloride, -iodide, -citrate, -hydroxide, -nitrate, -sulfate, -arylsulfonates, -alkylsulfonates, -acetylacetonate, bis(benzonitrile)palladium chloride, and potassium tetrachloro palladate.

22. The process as defined in claim 20, wherein the palladium compound is a compound from the group of bis(cyclooctadiene-1,5) (palladium (zero), tetra (triphenylphosphine) palladium (zero), and potassium tetracyano palladate.

23. The process as defined in claim 1, wherein the reaction is effected in the presence of a reducing agent capable of reducing the transition metal.

24. The process as defined in claim 23, wherein the reducing agent is an agent from the group of sodium borohydride, potassium borohydride, zinc powder, and magnesium.

25. The process as defined in claim 1, wherein the amount of transition metal is from about $10^{-4}$ to about 1 gram atom per liter.

26. The process as defined in claim 25, wherein the amount of transition metal is from about 0.005 to about 0.5 gram atom per liter.

27. The process as defined in claim 1, wherein the amount of a phosphine of the formula (I) is from about 0.5 to 2,000 moles per gram atom of transition metal.

28. The process as defined in claim 27, wherein the amount of a phosphine of formula (I) is from about 1 to about 30 moles per gram atom of transition metal.

29. The process as defined in claim 1, wherein the reaction is effected in the presence of an additive selected from the group consisting of a basic compound and a mixture of a basic compound and an acid.

30. The process as defined in claim 29, wherein the additive is selected from the group consisting of alkaline metal hydroxide, alkaline earth metal hydroxides, tertiary aliphatic amines, tertiary aromatic amines and phenolates.

31. The process as defined in claim 29, wherein the acid is a mineral acid of an element of the Groups IIIA, IVA, VA, VIA and VIIA of the periodic system.

32. The process as defined in claim 29, wherein the acid is a carbocyclic arylsulfonic or alkylsulfonic acid.

33. The process as defined in claim 29, wherein the additive is selected from the group consisting of alkaline carbonates, alkaline bicarbonates, sodium silicates and alkaline salts of phosphorus acid, phosphoric acid and arsenic acid.

34. The process as defined in claim 33, wherein the additive is sodium carbonate.

35. The process as defined in claim 1, wherein the reaction mixture comprises an organic water immiscible solvent.

36. The process as defined in claim 35, wherein the solvent is a solvent of the group of benzene, benzonitrile, acetophenone, ethyl ether, propyl ether, isopropyl ether, methylethylketone and propionitrile.

37. The process as defined in claim 1, wherein the reaction mixture further comprises an organic water miscible solvent.

38. The process as defined in claim 37, wherein the solvent is a solvent of the group of acetone, acetonitrile, dimethylether of diethylene glycol and dimethoxyethane, dioxane, tert. butanol, dimethyl acetamide, n-methyl pyrolidone and ethylene carbonate.

39. The process as defined in claim 1, wherein the reaction is performed at a temperature between about −20° C. and about 200° C.

40. The process as defined in claim 1, which comprises reacting isoprene with methanol whereby 1-methoxy-2,6-dimethyloctadiene-2,7 is formed.

41. The process as defined in claim 1, which comprises reacting butadiene with phenol whereby 1-phenoxyoctadiene-2,7 is formed.

42. The process as defined in claim 2, wherein the diene is a diene having 4 to about 8 carbon atoms.

43. The process as defined in claim 3, wherein the diene is selected from the group consisting of butadiene, isoprene, piperylene and dimethylbutadiene.

44. The process as defined in claim 2, which comprises reacting a sufficient amount of a compound of formula (II)

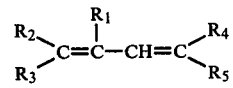

containing 4 to about 20 carbon atoms, wherein at least one of the substituents $R_1$, $R_2$, $R_3$, $R_4$ and $R_5$ is hydrogen and the remaining substituents $R_1$, $R_2$, $R_3$, $R_4$ and $R_5$ are the same or different and each represent hydrogen, alkyl having 1 to 5 carbon atoms or alkenyl having 3 to 5 carbon atoms with a telomerizing compound HOR, wherein R represents hydrogen, alkyl having 1 to about 20 carbon atoms, alkenyl having 3 to about 20 carbon atoms, aryl having 6 to about 20 carbon atoms, to form a reaction product containing a major portion of dimer derivatives of the compound of formula (II).

* * * * *